United States Patent
Wadgaonkar et al.

(10) Patent No.: US 9,133,089 B2
(45) Date of Patent: Sep. 15, 2015

(54) PROCESS FOR PREPARING A CROSS LINKING CATALYST FROM CASHEW NUT SHELL LIQUID

(71) Applicant: Council of Scientific & Industrial Research, New Delhi (IN)

(72) Inventors: Prakash Purushottam Wadgaonkar, Maharashtra (IN); Bhimrao Dhondiba Sarwade, Pune (IN); Bhausaheb Vilas Tawade, Pune (IN)

(73) Assignee: Counsel of Scientific & Industrial Research (IN)

( * ) Notice: Subject to any disclaimer, the term of this patent is extended or adjusted under 35 U.S.C. 154(b) by 0 days.

(21) Appl. No.: 14/363,204

(22) PCT Filed: Dec. 5, 2012

(86) PCT No.: PCT/IN2012/000794
§ 371 (c)(1),
(2) Date: Jun. 5, 2014

(87) PCT Pub. No.: WO2013/084248
PCT Pub. Date: Jun. 13, 2013

(65) Prior Publication Data
US 2014/0357891 A1    Dec. 4, 2014

(30) Foreign Application Priority Data
Dec. 5, 2011   (IN) .......................... 3497/DEL/2011

(51) Int. Cl.
*C07C 41/01* (2006.01)
*C07C 309/42* (2006.01)
*C07C 37/00* (2006.01)
*C07C 303/20* (2006.01)

(52) U.S. Cl.
CPC ............. *C07C 41/01* (2013.01); *C07C 37/003* (2013.01); *C07C 303/20* (2013.01); *C07C 309/42* (2013.01)

(58) Field of Classification Search
None
See application file for complete search history.

(56) References Cited

U.S. PATENT DOCUMENTS

| 5,202,355 A | 4/1993 | Nakatsu | |
| 6,552,107 B1 * | 4/2003 | Paul et al. | 524/158 |
| 2005/0038274 A1 * | 2/2005 | Chowdhury et al. | 556/404 |

FOREIGN PATENT DOCUMENTS

GB    2360524    * 9/2001

OTHER PUBLICATIONS

Kumar et al., Journal of Agricultural and Food Chemistry, American Chemical Society, vol. 50, Jan. 1, 2002, pp. 4705-4708.*
International Preliminary Report on Patentability, PCT/IN2012/000794, Council of Scientific & Industrial Research, Jun. 10, 2014.
International Search Report and Written Opinion of the International Searching Authority, PCT Application No. PCT/IN2012/000794, Council of Scientific & Industrial Research, Mar. 6, 2013.
Sethi, S.C. et al, Preparation & Properties of Ethers of 3-Pentadecylphenol, Indian Journal of Technology, New Dehli, vol. 2, Jan. 1, 1964, pp. 206-208.
de Sousa Rios, Maria Alexsandra et al., Thermal behavior of phosphorus derivatives of hydrogenated cardanol, Fuel Processing Technology, Elsevier BV, NL, vol. 96, Dec. 2, 2011, pp. 1-8.
Kumar, P. Phani, et al., Process for Isolation of Cardanol from Technical Cashew (Anacardium occidentale L.) Nut Shell Liquid, Journal of Agricultural and Food Chemistry, American Chemical Society, US, vol. 50, Jan. 1, 2002, pp. 4705-4708.
Sethi, S.C. et al., Relation of Structure to Surface-active Properties of Alkoxy-Alkylbenzene Sulphonates, Indian Journal of Technology, vol. 2, Jul. 1964, pp. 277-282.

* cited by examiner

*Primary Examiner* — Karl J Puttlitz
(74) *Attorney, Agent, or Firm* — McDonald Hopkins LLC

(57) ABSTRACT

A process for synthesis of sulfonated, arylated 3-pentadecyl phenol (cross linking catalyst) of formula I starting from Cashew Nut Shell Liquid. Formula I wherein R is benzenesulfonic acid; X is —SO3H, where n is 0 or 1; wherein the process steps comprises hydrogenating cardanol with 5% Pd/C in presence of lower alcoholic solvent at 70° C. under 600 psi hydrogen pressure to obtain 3-pentadecyl phenol; arylating 3-pentadecyl phenol to obtain 3-pentadecyl diphenyl ether; and sulfonating the 3-pentadecyl diphenyl ether to obtain compound of formula I.

8 Claims, No Drawings

PROCESS FOR PREPARING A CROSS LINKING CATALYST FROM CASHEW NUT SHELL LIQUID

TECHNICAL FIELD OF INVENTION

The present invention relates to sulfonated, alkylated/arylated 3-pentadecyl phenols, (cross linking catalysts) synthesized starting from 3-pentadecyl phenol obtained from Cashew Nut Shell Liquid (CNSL). A process for synthesis of the said catalysts is also described.

BACKGROUND & PRIOR ART

CNSL is a versatile byproduct of cashew industries. The versatility of CNSL results from the multiple industrial applications for CNSL based products. Further, a large number of value added chemical products have been synthesized starting from chemical compounds isolated from CNSL.

With the increasing emphasis on reducing industrial emissions and release of effluents resulting from chemical reactions, use of catalysts is increasingly in vogue. With a view to improve the efficiency of reaction and the productivity, various types of catalysts which are industry friendly are being evaluated and industrially made use of.

There are different types of catalysts. Noble & precious metals are well known to be used as catalysts. There are heterogeneous & homogeneous catalysts as well as electro catalysts & organo catalysts. Latest cross linking catalysts, in which two or more adjacent molecules join to form a bigger molecule such as cross linked polymer, are presently recognized as highly active and economically suitable as well as effective for industrial applications.

U.S. Pat. No. 6,552,107 discloses synthesis of dopant involving sulfonation of methyl ether of 3-pentadecyl phenol. Processes for preparation of methyl ether of hydrogenated 3-pentadecyl phenol using KOH/water, alcohol & dimethyl sulphate in alcohol and sulfonation of 3-pentadecyl phenol using 98% c. $H_2SO_4$ at 70-80° C. are described in this document.

US2002035215 titled "Alkylated aryl disulfonic acid catalysts for crosslinking polyethylene" discloses a highly active condensation catalyst suitable for the crosslinking of alkoxysilanyl polyolefins. The crosslinked polymeric compositions obtained as described herein are indicated for use as coatings for electrical cables and wires.

U.S. Pat. No. 2,324,300 describes sulfonation of phenols and phenolic ethers of CNSL, cardanol, urushiol, and several alkyl ethers of these phenols where preferably the alkyl group is C1-C5 carbon atoms and the preferred ethers include primary, secondary and tertiary alkyl ethers of the above named phenols. The products disclosed are described to be useful in the wetting and detergency of textiles.

US2007154730 titled "Method of cross-linking a filled polymer based on polyethylene" describes a method of cross-linking a composition comprising firstly a polyethylene-based silane-grafted polymer, and secondly a filler.

US2008/0097038 deals with a silane-crosslinkable polymer composition comprising (i) at least one silane-crosslinkable polymer, and (ii) a catalytic amount of at least one polysubstituted aromatic sulfonic acid of a disclosed formula of composition. The polymer is used in the form of a wire or cable insulation coating.

Crosslinking in polyethylene and polypropylene is important to improve the properties such as heat deformation resistance, chemical resistance, stress cracking, shrinkage, etc. There are different techniques viz; radical crosslinking initiated by peroxide and irradiation. These techniques have its disadvantages. Incorporation of vinyl silane during polymerization has several advantages compared to grafting technique.

OBJECTS OF THE INVENTION

The main object of the present invention is to provide the a process for preparation of Cross Linking Catalyst from CNSL.

Another object of the invention is to provide a process for preparation of sulfonated, alkylated/arylated 3-pentadecyl phenols, (cross linking catalysts) synthesized starting from 3-pentadecyl phenol obtained.

Still another object of the invention is to provide a single line process, going directly from the reactor to the extruder without going through grafting and/or compounding. One more object of the invention is to provide a process to provide a product that is very clean with uniform density and molecular weight distribution.

SUMMARY OF THE INVENTION

Accordingly the present invention provides a process for synthesis of sulfonated, alkylated/arylated 3-pentadecyl phenol (cross linking catalyst) of formula I from 3-pentadecyl phenol obtained from Cashew Nut Shell Liquid comprises:

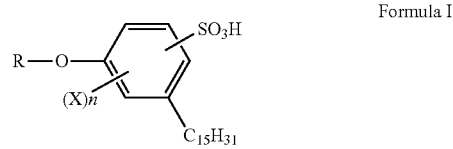

Formula I wherein R is selected from the group consisting of methyl or benzenesulfonic acid;
X is —$SO_3H$, where n is 0 or 1;
with a proviso when n is 1, R is methyl wherein the process steps comprising;
a) hydrogenating cardanol with 5% Pd/C in presence of lower alcoholic solvent at 70° C. under 600 psi hydrogen pressure to obtain 3-pentadecyl phenol;
b) alkylating/arylating 3-pentadecyl phenol to obtain arylated or alkylated 3-pentadecyl phenol and
c) sulfonating the alkylated/arylated 3-pentadecyl phenol to obtain sulfonated, alkylated/arylated 3-pentadecyl phenol of formula I.

In an embodiment of the present invention wherein, the sulfonated, alkylated/arylated 3-pentadecyl phenol of formula I is selected from benzene-1-methoxy-3-pentadecyl-4, 6-disulfonic acid and 4-4'-disulfonic acid-2-pentadecyl diphenyl ether.

The process for synthesis of cross linking catalyst, 4-4'-disulfonic acid-2-pentadecyl diphenyl ether from 3-pentadecyl phenol obtained from Cashew Nut Shell Liquid, wherein the process comprises:
a) hydrogenating cardanol with 5% Pd/C in presence of lower alcoholic solvent selected from a group consisting of methanol, ethanol and isopropanol at 70° C. under 600 psi hydrogen pressure to obtain 3-pentadecyl phenol;
b) refluxing 3-pentadecyl phenol with alkali metal hydroxide in presence of a polar and non-polar solvent for about 7-8 hrs followed by removal of water from the mixture azeotropically and distilling off the solvent to obtain the alkali metal salt of 3-pentadecyl phenol;
c) arylating alkali metal salt of 3-pentadecyl phenol in presence of bromobenzene and copper powder in a solvent to obtain 1-pentadecyl-3-phenoxy benzene,
d) sulphonating 1-pentadecyl-3-phenoxy benzene with oleum at about 10° C. for 25-35 min followed by raising the temperature to about 70° C. for about 6-8 h to obtain 4-4'-disulfonic acid-2-pentadecyl diphenyl ether.

In an embodiment of the present invention wherein the polar and non-polar solvent used in step b) are dimethyl acetamide (DMAC) and toluene respectively.

In another embodiment of the present invention wherein the alkali metal salt of 3-pentadecyl phenol is potassium salt.

In still another embodiment of the present invention wherein the solvent used in step c) is dimethyl acetamide.

In yet another embodiment of the present invention wherein, the arylation reaction is carried at about 150° C.

The process for synthesis of cross linking catalyst, benzene-1-methoxy-3-pentadecyl-4,6-disulfonic acid from 3-pentadecyl phenol obtained from Cashew Nut Shell Liquid, wherein the process comprises:
a) hydrogenating cardanol with 5% Pd/C in presence of lower alcoholic solvent selected from a group consisting of methanol, ethanol and isopropanol at 70° C. under 600 psi hydrogen pressure to obtain 3-pentadecyl phenol;
b) alkylating 3-pentadecyl phenol with methyl iodide in polar aprotic solvent to obtain 3-pentadecyl anisole; and
c) treating 3-pentadecyl anisole with concentrated $H_2SO_4$ at about 10° C. for 25-35 min followed by raising the temperature to about 70° C. for about 6-8 h to obtain benzene-1-methoxy-3-pentadecyl-4,6-disulfonic acid.

In an embodiment of the present invention wherein, the polar aprotic solvent is selected from DMF, acetone, THF, DMSO.

Accordingly the present invention also provides the compound 4-4'-disulfonic acid-2-pentadecyl diphenyl ether from 3-pentadecyl phenol of formula 1

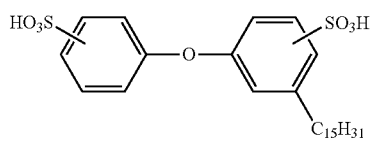

Formula 1

The present invention relates to industrially useful crosslinking catalysts for silane functionalized polyolefins obtained from CNSL. While some of the catalysts disclosed herein are known in prior art, the process for obtaining these catalysts from CNSL, according to the present invention, describes a single line process for the synthesis of disulphonic acids starting from CNSL, however is not known.

DETAILED DESCRIPTION

The invention will now be described in detail in connection with certain preferred and optional embodiments, so that various aspects thereof may be more fully understood and appreciated and briefly described as follows.

Disulfonic acids are highly effective crosslinking catalysts at a very low concentration in the silane functionalized polyolefin composition.

The present invention discloses the synthesis of a sulfonated, alkylated/arylated 3-pentadecyl phenol of formula I, also referred as crosslinking catalysts starting from 3-pentadecyl phenol which is obtained from cashew nut shell liquid (CNSL), an inexpensive and a renewable resource material.

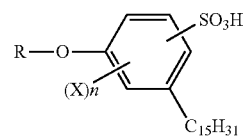

Formula-I wherein R is selected from the group consisting of methyl or benzenesulfonic acid group;
X is —$SO_3H$, where n is 0 or 1;
with a proviso when n is 1, R is methyl.

Accordingly the invention in its preferred embodiment discloses a process for synthesis of cross linking catalyst of formula I from 3-pentadecyl phenol obtained from Cashew Nut Shell Liquid comprises:

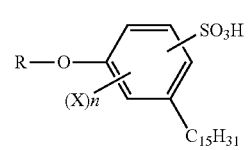

Formula I wherein R is selected from the group consisting of methyl or benzenesulfonic acid;
X is —$SO_3H$, where n is 0 or 1;
with a proviso when n is 1, R is methyl.
a) hydrogenating cardanol with 5% Pd/C in presence of lower alcoholic solvent at 70° C. under 600 psi hydrogen pressure to obtain 3-pentadecyl phenol;
b) alkylating/arylating 3-pentadecyl phenol to obtain arylated or alkylated 3-pentadecyl phenol; and
c) sulfonating the alkylated/arylated 3-pentadecyl phenol to obtain sulfonated, alkylated/arylated 3-pentadecyl phenol.

The sulfonated, alkylated/arylated 3-pentadecyl phenol of formula I according to the invention is selected from benzene-1-methoxy-3-pentadecyl-4,6-disulfonic acid and 4-4'-disulfonic acid-2-pentadecyl diphenyl ether.

Thus the present invention describes the synthesis of benzene-1-methoxy-3-pentadecyl-4,6-disulfonic acid and 4-4'-disulfonic acid-2-pentadecyl diphenyl ether, which is potentially used as crosslinking catalysts in the silane functionalized polyolefin compositions, from 3-pentadecyl phenol which is obtained from cashew nut shell liquid (CNSL).

In the process of the instant invention, 3-pentadecyl phenol is prepared by hydrogenation of cardanol in presence of a reducing agent such as Pd/C, Pt, Raney Ni, preferably, 5% Pd/C and in presence of lower alcoholic solvent at 70° C. under 600 psi hydrogen pressure. 3-pentadecyl phenol so obtained is further used to prepare cross linking catalysts.

Accordingly, in a preferred embodiment, the synthesis of 4-4'-disulfonic acid-2-pentadecyl diphenyl ether comprises:
1. hydrogenating cardanol with 5% Pd/C in presence of lower alcoholic solvent at 70° C. under 600 psi hydrogen pressure to obtain 3-pentadecyl phenol;
2. refluxing 3-pentadecyl phenol with alkali metal hydroxide in presence of a polar and non-polar solvent for about 7-8 hrs followed by removal of water from the mixture azeotropically and distilling off the solvent to obtain the alkali metal salt of 3-pentadecyl phenol;

3. arylating alkali metal salt of 3-pentadecyl phenol in presence of bromobenzene and copper powder in presence of a solvent to obtain 1-pentadecyl-3-phenoxy benzene; and 4. sulphonation of 1-pentadecyl-3-phenoxy benzene with oleum at about 10° C. for 25-35 min followed by raising the temperature to about 70° C. for about 6-8 h to obtain 4-4'-disulfonic acid-2-pentadecyl diphenyl ether.

According to the process steps described above, to a two necked round bottomed flask fitted with a reflux condenser is added 3-pentadecyl phenol, potassium hydroxide, dimethyl acetamide (DMAC) and toluene. The reaction mixture is refluxed for 7 h and the by-product water formed is removed from the reaction mixture azeotropically. After completion of the reaction, the solvent is distilled off and dried under reduced pressure to obtain potassium salt of 3-pentadecyl phenol.

Into the round bottom flask containing potassium salt of 3-pentadecyl phenol is added bromobenzene followed by Cu powder and in a solvent, DMAc (dimethyl acetamide). The reaction mixture is heated at 150° C. for 6 h. After completion of the reaction, the obtained dark colored reaction mixture is poured into water and the Cu salts are removed by filtration. The filtrate is extracted in a solvent, washed with water and dried, purified to obtain arylated product, 1-pentadecyl-3-phenoxybenzene.

Further to a round bottomed flask fitted with a magnetic stirring bar and a dropping funnel is added 1-pentadecyl-3-phenoxybenzene. The content of the flask is chilled in a cooling bath. Oleum is added drop wise over a period of about 30 minutes with stirring so as to maintain an internal temperature of about 10° C. After all the oleum has been added, the cooling bath is removed, and the reaction mixture is allowed to attend the room temperature and continued the reaction for about 6-8 h. The mixture is poured into ice-cooled deionized water with stirring, extracted with ethyl acetate to remove unreacted 1-pentadecyl-3-phenoxybenzene. The aqueous layer is neutralized with sodium bicarbonate and cooled to about 10° C. for about 3 h; filtered, diluted with n-butanol, concentrated to obtain sulfonated, arylated 3-pentadecyl phenol, 4-4'-disulfonic acid-2-pentadecyl diphenyl ether. The material is further washed with methanol to remove any coloured impurities and purified to obtain the pure compound.

The process is described in Scheme 1 below:

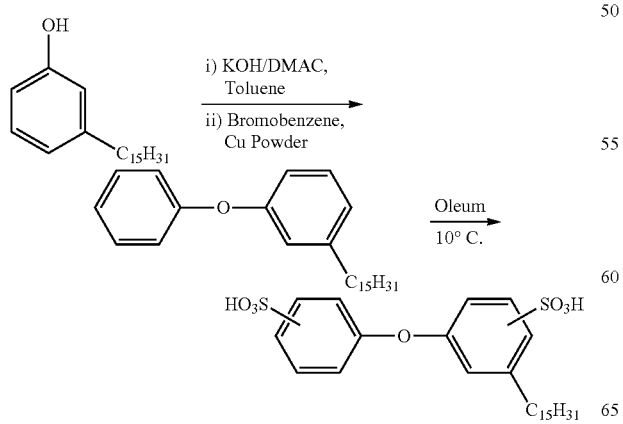

Synthesis of 4-4'-disulfonic acid-2-pentadecyl diphenyl ether

In another embodiment, the synthesis of benzene-1-methoxy-3-pentadecyl-4,6-disulfonic acid comprises:

1. hydrogenating cardanol with 5% Pd/C in presence of lower alcoholic solvent at 70° C. under 600 psi hydrogen pressure to obtain 3-pentadecyl phenol;

2. alkylating/3-pentadecyl phenol in polar aprotic solvent to obtain 3-pentadecyl anisole; and 3. treating 3-pentadecyl anisole with concentrated H2SO4 at about 10° C. for 25-35 min followed by raising the temperature to about 70° C. for about 6-8 h to obtain benzene-1-methoxy-3-pentadecyl-4,6-disulfonic acid.

The polar aprotic solvent used in step (ii) is selected from DMF, acetone, THF, DMSO and the like.

To a two necked round bottomed flask with a reflux condenser is added 3-pentadecyl phenol, DMSO, sodium hydroxide followed by dropwise addition of alkylating agent such as methyl iodide with constant stirring at room temperature. The stirring is continued for about 6-8 hrs. The reaction mixture is then poured into deionized water and the organic matter is extracted in diethyl ether, separated the organic layer, washed with water and dried, purified to obtain 3-pentadecyl anisole.

To a round bottomed flask fitted with a magnetic stirring bar and a dropping funnel is added 3-pentadecyl anisole. The content of the flask is chilled in a cooling bath followed by drop wise addition of concentrated sulfuric acid over a period of about 30 minutes with stirring so as to maintain an internal temperature of about 10° C. After all the sulfuric acid had been added, the cooling bath is removed, and the reaction mixture is further heated to maintain a temperature of about 70° C. for about 6-8 h. The mixture is cooled to room temperature and poured into ice-cooled deionized water with stirring, extracted with ethyl acetate to remove unreacted 3-pentadecyl anisole as an ethyl acetate solution. The aqueous layer is neutralized with sodium bicarbonate and cooled to about 10° C. for about 3 h. The precipitated sodium sulfate is filtered off, and the filtrate is diluted with n-butanol, concentrated under reduced pressure, filtered to obtain the desired sulphonated, alkylated 3-pentadecyl phenol of formula I, benzene-1-methoxy-3-pentadecyl-4,6-disulfonic acid.

The process is described in Scheme 2 below:

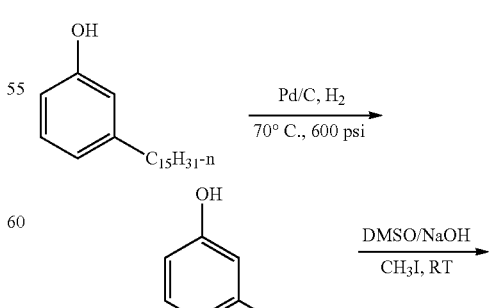

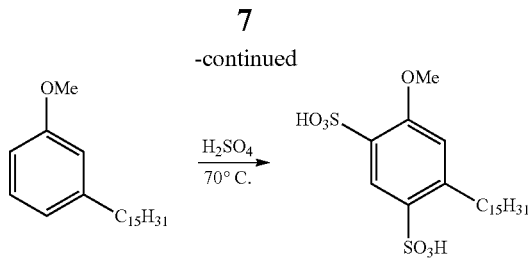

Synthesis of benzene-1-methoxy-3-pentadecyl-4,6-disulfonic acid

There are many advantages to the processes described herein above. It is a single line process. It can go directly from the reactor to the extruder without going through grafting and/or compounding. This process also provides a product that is very clean with uniform density and molecular weight distribution.

The process described herein, starting from cardanol to sulphonated 1-pentadecyl-3-phenoxybenzene or benzene-1-methoxy-3-pentadecyl-4,6-disulfonic acid, which are identified as potential cross linking catalysts for silane functionalized polyolefins, is novel and of the high industrial utility.

The invention can be better understood by the following non-limiting examples. The examples given are mere an illustration of the instant invention and should not be construed as limiting the scope of the present invention in any manner.

EXAMPLES

Example 1

Conversion of cardanol to 3-pentadecyl phenol

Cardanol (500 g, 1.64 mol) was dissolved in isopropanol (2 L) and was hydrogenated in presence of 5% Pd/C (1.5 g) catalyst at 70° C. in a Parr autoclave under 600 psi hydrogen pressure. When no more hydrogen absorption was noticed, the hydrogenation was stopped. The reaction mixture was filtered to remove Pd/C. The solvent was evaporated to obtain crude product. Pure 3-pentadecylphenol was obtained after recrystallization from hexane. Yield 480 g, (95%), MP: 50-51° C.

Example 2

Synthesis of 3-pentadecyl anisole

Into a two-liter round bottomed flask was placed dimethyl sulfoxide (500 mL), 3-pentadecyl phenol (100.0 g, 0.33 mol) and sodium hydroxide (73.55 g, 1.31 mol). To this mixture methyl iodide (93.5 g, 0.66 mol) was added drop wise with stirring at room temperature. After the addition, the reaction mixture was stirred for further 6 h. Then the reaction mixture was poured into deionized water (1.5 liters). The organic material was extracted by addition of diethyl ether. The diethyl ether layer was separated, washed with water, dried over anhydrous sodium sulfate, and finally evaporated to afford the crude product as a viscous liquid. This material was purified by silica gel column chromatography using petroleum ether as the eluent to obtain 3-pentadecyl anisole Yield 104.6 g (97%), MP 27-28° C.

Example 3

Synthesis of 1-pentadecyl-3-phenoxybenzene

Into a 1000 mL two necked round bottomed flask fitted with Dean and Stark assembly with a reflux condenser were taken 3-pentadecyl phenol (100.0 g, 0.33 mol), potassium hydroxide (22.06 g, 0.39 mol), dimethyl acetamide (DMAC) (300 mL0 and toluene (150 mL). The reaction mixture was refluxed for 7 h and the by-product water formed was removed from the reaction mixture azeotropically. After completion of the reaction, the solvent was distilled off and the dark sticky product was dried under reduced pressure. The compound obtained was potassium salt of 3-pentadecyl phenol.

Into a 1000 mL round bottom flask containing potassium salt of 3-pentadecyl phenol (111.0 g, 0.32 mol) was added bromobenzene (50.88 g, 0.32 mol) followed by Cu powder (2.22 g, 2 wt %) and DMAc (150 mL). The reaction mixture was heated at 150° C. for 6 h. After completion of the reaction, the obtained dark colored reaction mixture was poured into water (500 mL); the Cu salts were removed by filtration. The filtrate was extracted with ethyl acetate (2×300 mL), washed with saturated aqueous sodium chloride solution (2×100 mL) followed by water (3×100 mL) and dried over sodium sulfate. Solvent evaporation yielded crude 1-pentadecyl-3-phenoxybenzene. Pure 1-pentadecyl-3-phenoxybenzene was obtained after silica gel (60-120 mesh) column chromatography (eluent: pet ether). Yield 70 g (57%); MP 32° C.

Example 4

Synthesis of benzene-1-methoxy-3-pentadecyl-4,6-disulfonic acid

Into a 500 mL round bottomed flask fitted with a magnetic stirring bar and a dropping funnel was added 3-pentadecyl anisole (56.0 g, 0.18 mol). The content of the flask were chilled in a cooling bath. Concentrated sulfuric acid (46.5 g, 0.48 mol) was added drop wise over a period of about 30 minutes with stirring so as to maintain an internal temperature of about 10° C. After all the sulfuric acid had been added, the cooling bath was removed, and the reaction mixture was heated to maintain a temperature of about 70° C. for about 6 h. Then the mixture was cooled to room temperature and poured into ice-cooled deionized water (500 mL) with stirring. The mixture was extracted with ethyl acetate (3×100 mL) to remove unreacted 3-pentadecyl anisole as an ethyl acetate solution. The aqueous layer was neutralized with sodium bicarbonate and cooled to about 10° C. for about 3 h. The precipitated sodium sulfate was filtered off, and the filtrate was diluted with n-butanol (500 mL). The n-butanol solution was concentrated on a rotary evaporator under reduced pressure. Methanol (500 mL) was added to the residual material whereupon some more sodium sulfate precipitated out which was removed by filtration. The process of adding methanol, concentration under reduced pressure, subsequent addition of more methanol, and filtration was done two more times to ensure complete removal of sodium sulfate. The filtrate resulting finally was evaporated under reduced pressure to obtain crude disodium salt of benzene-1-methoxy-3-pentadecyl-4,6-disulfonic acid. This material was washed with hot ethanol (3×100 mL) to remove colored impurities.

The clarified disodium salt from above was dissolved in deionized water and the solution was passed through a column packed with Tulsion $H^+$ ion exchange resin (previously purified by washing with hot distilled water). The elute from the column was collected and removed the water under reduced pressure to get the desired product. Yield 6.5 g (40%).

Example 5

Sulfonation of 1-pentadecyl-3-phenoxybenzene

Into a 500 mL round bottomed flask fitted with a magnetic stirring bar and a dropping funnel was added 1-pentadecyl-3-phenoxybenzene (10.0 g, 0.18 mol). The content of the flask were chilled in a cooling bath. Oleum (21.5 g, 12.57 mL) was added drop wise over a period of about 30 minutes with stirring so as to maintain an internal temperature of about 10° C. After all the oleum had been added, the cooling bath was removed, and the reaction mixture was allowed to attend the room temperature and continued the reaction for about 6 h. Then the mixture was poured into ice-cooled deionized water (500 mL) with stirring. The mixture was extracted with ethyl acetate (3×100 mL) to remove unreacted 1-pentadecyl-3-phenoxybenzene. The aqueous layer was neutralized with sodium bicarbonate and cooled to about 10° C. for about 3 h. The precipitated sodium sulfate was filtered off, and the filtrate was diluted with n-butanol (100 mL). The n-butanol solution was concentrated on a rotary evaporator under reduced pressure. Methanol (500 mL) was added to the residual material whereupon some more sodium sulfate precipitated out which was removed by filtration. The process of adding methanol, concentration under reduced pressure, subsequent addition of more methanol, and filtration was done two more times to ensure complete removal of sodium sulfate. The filtrate resulting finally was evaporated under reduced pressure to obtain crude disodium salt of 1-pentadecyl-3-phenoxybenzene. This material was washed with hot ethanol (3×100 mL) to remove colored impurities.

The clarified disodium salt from above was dissolved in deionized water and the solution was passed through a column packed with Tulsion H$^+$ ion exchange resin (previously purified by washing with hot distilled water). The elute from the column was collected and removed the water under reduced pressure to get the desired product. The obtained crude product was purified by column chromatography (eluent: ethyl acetate: methanol). Yield 6.0 g.

ADVANTAGES OF INVENTION

1. The process disclosed in a single line process, going directly from the reactor to the extruder without going through grafting and/or compounding.
2. This process also provides a product that is very clean with uniform density and molecular weight distribution
3. This disclosure describes the synthesis of a crosslinking catalyst starting from 3-pentadecyl phenol which is obtained from cashew nut shell liquid (CNSL), an inexpensive and a renewable resource material.

We claim:
1. A process for synthesis of sulfonated, arylated 3-pentadecyl phenol of formula I from Cashew Nut Shell Liquid comprises:

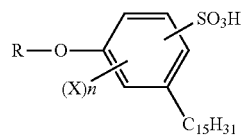

Formula I wherein R is benzenesulfonic acid;
X is —SO3H, where n is 0 or 1;
wherein the process steps comprise:
a) hydrogenating cardanol with 5% Pd/C in presence of alcoholic solvent at 70° C. under 600 psi hydrogen pressure to obtain 3-pentadecyl phenol;
b) arylating 3-pentadecyl phenol to obtain arylated 3-pentadecyl phenol; and
c) sulfonating the arylated 3-pentadecyl phenol to obtain sulfonated, arylated 3-pentadecyl phenol of formula I.

2. The process as claimed in claim 1, wherein, the sulfonated, arylated 3-pentadecyl phenol of formula I is 4-4'-disulfonic acid-3-pentadecyl diphenyl ether.

3. The process for synthesis of 4-4'-disulfonic acid 3-pentadecyl diphenyl ether from 3-pentadecyl phenol obtained from Cashew Nut Shell Liquid as claimed in claim 2, wherein the process comprises:
a) hydrogenating cardanol with 5% Pd/C in presence of alcoholic solvent selected from the group consisting of methanol, ethanol and isopropanol at 70° C. under 600 psi hydrogen pressure to obtain 3-pentadecyl phenol;
b) refluxing 3-pentadecyl phenol with alkali metal hydroxide in presence of a polar and a non-polar solvent for about 7-8 hours followed by removal of water from the mixture azeotropically and distilling off the solvent to obtain the alkali metal salt of 3-pentadecyl phenol;
c) arylating alkali metal salt of 3-pentadecyl phenol in presence of bromobenzene and copper powder in a solvent to obtain 1-pentadecyl-3-phenoxy benzene; and
d) sulphonating 1-pentadecyl-3-phenoxy benzene with oleum at about-10° C. for 25-35 minutes followed by raising the temperature to about 70° C. for about 6-8 hours to obtain 4-4'-disulfonic acid-3-pentadecyl diphenyl ether.

4. The process according to claim 3, wherein the polar and non-polar solvent in step b) are dimethyl acetamide (DMAC) and toluene respectively.

5. The process according to claim 3, wherein the alkali metal salt of 3-pentadecyl phenol is potassium salt.

6. The process according to claim 3, wherein the solvent in step c) is dimethyl acetamide.

7. The process according to claim 3, wherein, the arylation reaction is carried out at about 150° C.

8. A compound 4-4'-disulfonic acid-3-pentadecyl diphenyl ether of formula 1

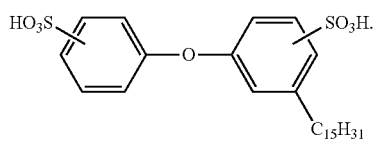

Formula 1

* * * * *